(12) United States Patent
Govari et al.

(10) Patent No.: US 12,566,595 B2
(45) Date of Patent: Mar. 3, 2026

(54) SYSTEMS AND METHODS FOR GENERATING ABLATION PROGRAMMING LANGUAGES AND ABLATION SYSTEM CONFIGURATIONS

(71) Applicant: BIOSENSE WEBSTER (ISRAEL) LTD., Yokneam (IL)

(72) Inventors: Assaf Govari, Haifa (IL); Andres Claudio Altmann, Haifa (IL); Ella Ozeri, Binyamina (IL); Dayan Siton, Pardes Han-Karkur (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1134 days.

(21) Appl. No.: 17/402,969

(22) Filed: Aug. 16, 2021

(65) Prior Publication Data

US 2023/0048486 A1     Feb. 16, 2023

(51) Int. Cl.
| | |
|---|---|
| *G06F 8/38* | (2018.01) |
| *A61B 17/00* | (2006.01) |
| *A61B 18/00* | (2006.01) |
| *A61B 18/14* | (2006.01) |
| *G06F 3/04847* | (2022.01) |
| *G06F 8/30* | (2018.01) |
| *G16H 20/30* | (2018.01) |
| *G16H 20/40* | (2018.01) |

(Continued)

(52) U.S. Cl.
CPC ............ *G06F 8/38* (2013.01); *A61B 18/1492* (2013.01); *G06F 8/313* (2013.01); *G16H 20/30* (2018.01); *G16H 20/40* (2018.01); *G16H 40/40* (2018.01); *G16H 40/67* (2018.01); *G16H 50/20* (2018.01); *A61B* *2017/00199* (2013.01); *A61B 2018/00577* (2013.01); *A61B 2018/00613* (2013.01); *A61B 2018/00702* (2013.01); *A61B 2018/00761* (2013.01); *G06F 3/04847* (2013.01)

(58) Field of Classification Search
None
See application file for complete search history.

(56) References Cited

U.S. PATENT DOCUMENTS

| | | | | |
|---|---|---|---|---|
| 5,390,314 | A | * 2/1995 | Swanson | ............. G06F 9/45512 |
| | | | | 717/138 |
| 6,216,034 | B1 | 4/2001 | Hofmann | |

(Continued)

FOREIGN PATENT DOCUMENTS

EP          3139997 A2     3/2017

OTHER PUBLICATIONS

European Search report for corresponding EPA No. 22190344.6 dated Jan. 2, 2023.

*Primary Examiner* — Qing Chen
(74) *Attorney, Agent, or Firm* — Clayton, McKay & Bailey, PC

(57) ABSTRACT

A method includes generating an ablation programming language, which defines commands for (i) setting ablation protocol parameters and respective values, (ii) setting a configuration of an ablation system, (iii) applying automatic logic that relates the ablation protocol parameters and the values to the configuration of the ablation system, and (iv) generating one or more graphical user interfaces (GUIs) showing one or more of the parameters of the ablation protocol and the system configuration. The ablation programming language is provided for subsequent use with the ablation system.

5 Claims, 3 Drawing Sheets

(51) Int. Cl.
    *G16H 40/40*       (2018.01)
    *G16H 40/67*       (2018.01)
    *G16H 50/20*       (2018.01)

(56)            References Cited

U.S. PATENT DOCUMENTS

| 6,681,386 | B1* | 1/2004 | Amin ................. G06F 9/45512 |
| | | | 717/136 |
| 7,991,559 | B2 | 8/2011 | Dzekunov |
| 8,234,620 | B1* | 7/2012 | Bychkov ................... G06F 8/00 |
| | | | 717/103 |
| 2013/0185698 | A1* | 7/2013 | Banerjee ................... G06F 8/75 |
| | | | 717/114 |
| 2014/0201669 | A1 | 7/2014 | Liu et al. |
| 2015/0327944 | A1 | 11/2015 | Neal, II |
| 2018/0071014 | A1 | 3/2018 | Neal |
| 2020/0201669 | A1 | 6/2020 | Hwang |
| 2020/0237425 | A1 | 7/2020 | Laughner |

* cited by examiner

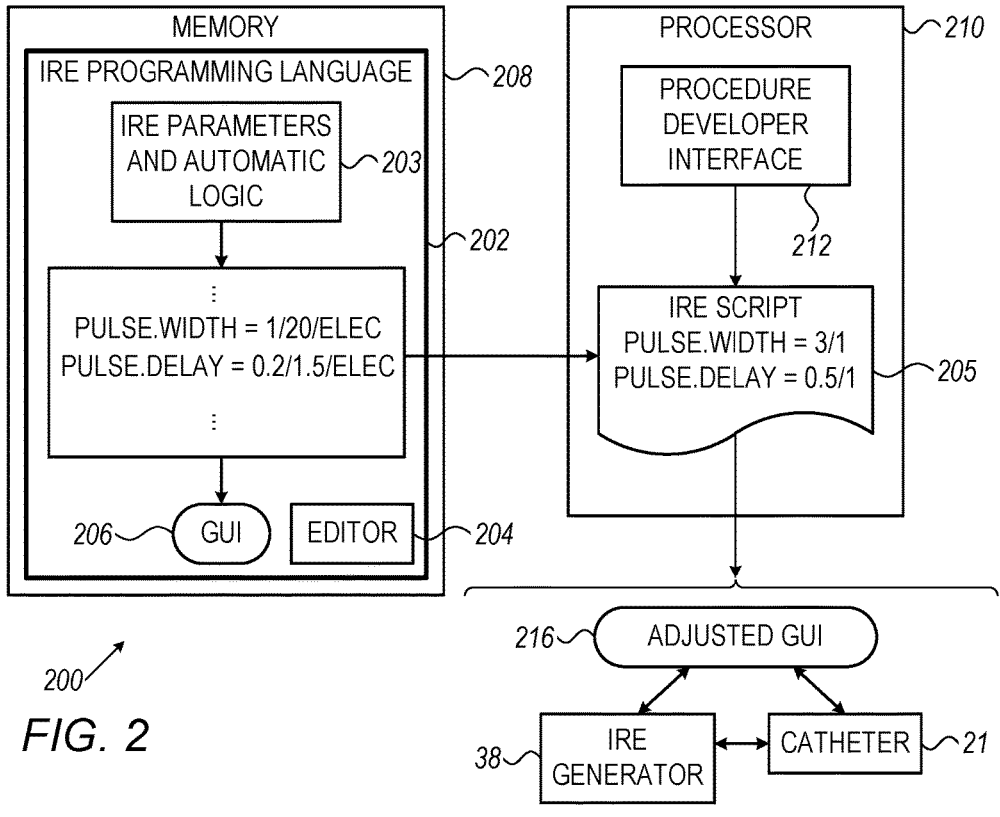
*FIG. 2*
*FIG. 3*
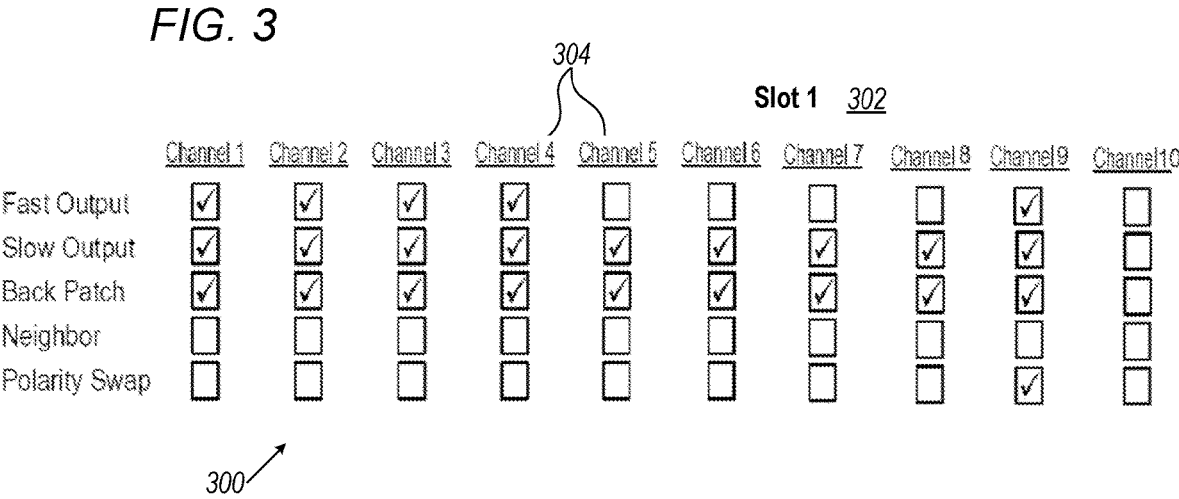

| 7 | 10 | 30 |
|---|---|---|
| # Pulses in train | # Bursts | # Burst cycle length (ms) |
| 3 | 0.5 | 400 |
| Pulse width(µs) | Pos/Neg pulse delay (µs) | Voltage (V) |

*400*

Generate IRE language ~502

Upload IRE parameters, automatic logic, editor, and GUIs ~504

Generate IRE script ~505

Using script, generate IRE protocol and system configuration shown on GUIs ~506

Using GUIs, set and/or adjust IRE protocol entrees and/or system configuration ~508

SYSTEMS AND METHODS FOR GENERATING ABLATION PROGRAMMING LANGUAGES AND ABLATION SYSTEM CONFIGURATIONS

FIELD OF THE INVENTION

The present invention relates generally to invasive ablation, and particularly to generating ablation protocols and system configurations.

BACKGROUND OF THE INVENTION

Methods of controlling irreversible electroporation (IRE) have been previously proposed in the patent literature. For example, U.S. Pat. No. 7,991,559 describes techniques for computerized electroporation. An electroporation apparatus may be controlled according to one of a plurality of previously-saved, user-defined processing protocols. A processing log associated with a processing protocol may be generated, and the processing log may include patient or sample specific information. The processing log or a summary of the processing log may be exported to a user. Interactive instructions may be provided to a user. Those instructions may correspond to one or more steps of a processing protocol.

As another example, U.S. Patent Application Publication No. 2018/0071014 describes a treatment device and method for delivering electrical pulses capable of creating irreversible electroporation. The system may include a bipolar probe with open or closed perfusion with the purpose of controlling the electrical conductivity rise to eliminate electrical arcing, without significantly altering the electric field distribution and treatment zone. This invention may include perfusion together with the delivery of specific or customized pulse parameters to achieve clinically acceptable ablation sizes using a bipolar probe with while reducing the overall risk of arcing or system failure.

SUMMARY OF THE INVENTION

An embodiment of the present invention that is described hereinafter provides a method including generating an ablation programming language, which defines commands for (i) setting ablation protocol parameters and respective values, (ii) setting a configuration of an ablation system, (iii) applying automatic logic that relates the ablation protocol parameters and the values to the configuration of the ablation system, and (iv) generating one or more graphical user interfaces (GUIs) showing one or more of the parameters of the ablation protocol and the system configuration. The ablation programming language is provided for subsequent use with the ablation system.

In some embodiments, the automatic logic specifies one or more interdependencies between the values of the ablation protocol. In other embodiments, the automatic logic specifies one or more limits on the values of the ablation protocol.

In some embodiments, at least one of the generated GUIs is also configured to receive user input for setting the parameters of the ablation protocol or the system configuration.

In some embodiments, the ablation is one of irreversible electroporation (IRE) and radiofrequency (RF) ablation.

There is additionally provided, in accordance with another embodiment of the present invention, a method, including using an ablation programming language, generating a script including a set of commands that (i) generate an ablation protocol and a compatible system configuration and (ii) adjust one or more graphical user interfaces (GUIs) showing the parameters of the ablation protocol and the system configuration. Using the one or more GUIs, values are entered for at least one of the parameters of the ablation protocol and the system configuration.

In some embodiments, the method further includes performing ablation according to the generated ablation protocol and system configuration.

In an embodiment, entering the parameters of the ablation protocol includes entering at least one of a power, a waveform, and a duration of ablation pulses in the ablation protocol.

In another embodiment, entering the values for the system configuration includes at least one of selecting catheter electrodes, selecting output channels of an ablation generator, and selecting interconnects between the catheter electrodes and the output channels.

There is further provided, in accordance with another embodiment of the present invention, a system including a memory and a processor. The memory is configured to store an ablation programming language. The processor is configured to: (a) upload the ablation programming language from the memory, (b) using the ablation programming language, generate a script including a set of commands that (i) generate an ablation protocol and a compatible system configuration and (ii) adjust one or more graphical user interfaces (GUIs) showing the parameters of the ablation protocol and the system configuration, and (c) using the one or more GUIs, enter values for at least one of the parameters of the ablation protocol and the system configuration.

There is furthermore provided, in accordance with another embodiment of the present invention, a computer software product, the product including a tangible non-transitory computer-readable medium in which program instructions are stored, which instructions, when read by one or more processors, cause the one or more processors to: (a) generate an ablation programming language, which defines commands for (i) setting ablation protocol parameters and respective values, (ii) setting a configuration of an ablation system, (iii) applying automatic logic that relates the ablation protocol parameters and the values to the configuration of the ablation system, and (iv) generating one or more graphical user interfaces (GUIs) showing one or more of the parameters of the ablation protocol and the system configuration, and (b) provide the ablation programming language for subsequent use with the ablation system.

BRIEF DESCRIPTION OF THE DRAWINGS

The present invention will be more fully understood from the following detailed description of the embodiments thereof, taken together with the drawings in which:

FIG. 2 is a block diagram schematically showing generation of a script and a graphical user interface (GUI), using an IRE programming language, in accordance with an exemplary embodiment of the present invention;

FIG. 3 is an example of a GUI for system configuration, where the GUI was generated using the IRE programming language of FIG. 2, in accordance with an exemplary embodiment of the present invention;

DETAILED DESCRIPTION OF EMBODIMENTS

Overview

Figure 1:
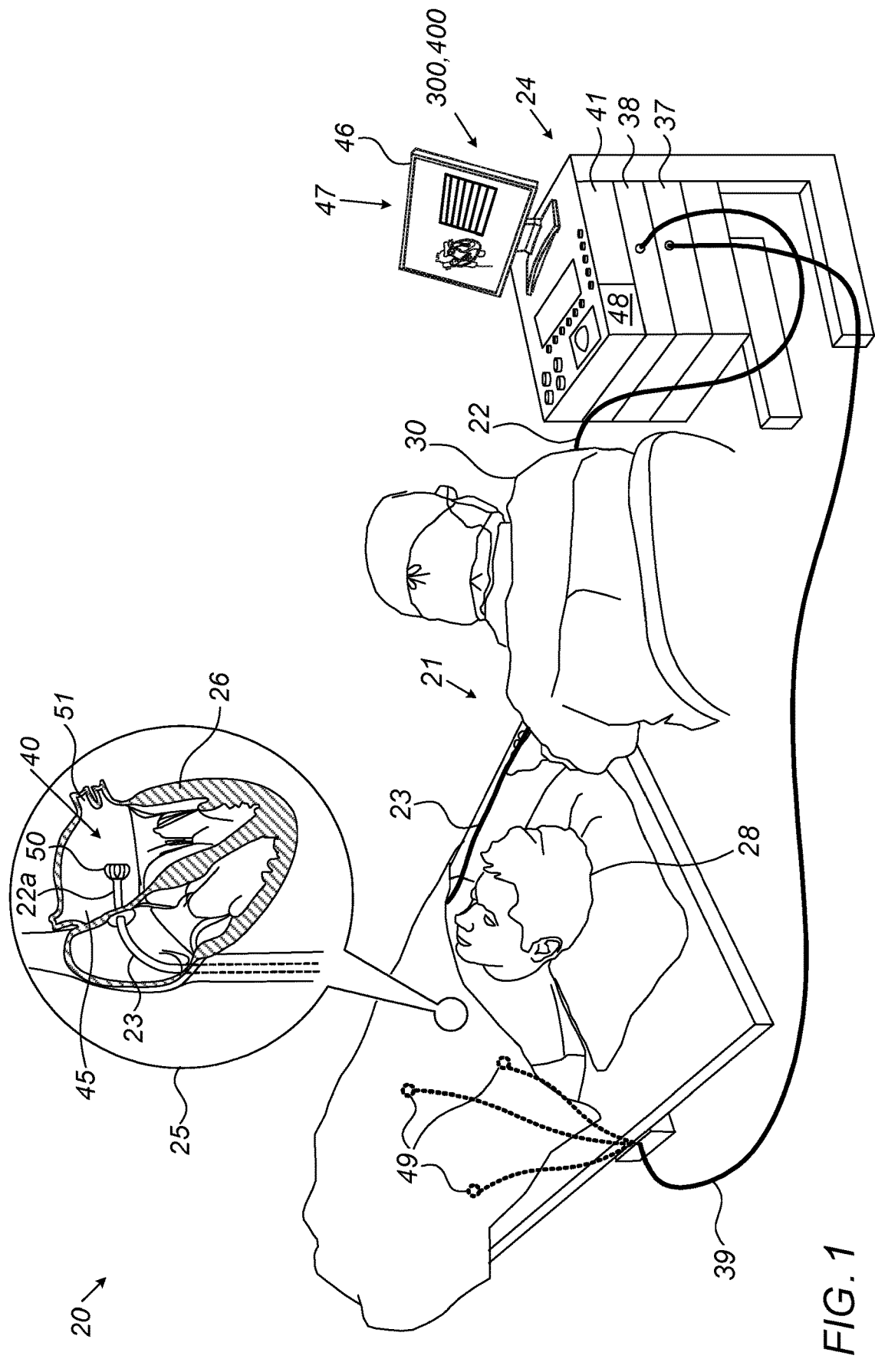
FIG. 1 is a schematic, pictorial illustration of a catheter-based irreversible electroporation (IRE) system, in accordance with an exemplary embodiment of the present invention.

Irreversible electroporation (IRE), also called Pulsed Field Ablation (PFA), may be used as an invasive therapeutic modality to kill tissue cells by subjecting them to high-voltage pulses. Specifically, IRE pulses have a potential use to kill myocardium tissue cells in order to treat cardiac arrhythmia. Cellular destruction occurs when the transmembrane potential exceeds a threshold, leading to cell death and thus the development of a tissue lesion. Therefore, of particular interest is the use of high-voltage bipolar electric pulses (e.g., using a selected set of pair of electrodes in contact with tissue) to generate high electric fields (e.g., above a certain threshold) to kill tissue cells between the electrodes.

Setting up an IRE procedure typically involves assigning values to a large number of inter-related parameters. Some examples of parameters are pulse type, pulse duration, delay between positive and negative pulses, pulse amplitude, number of pulses in a train, number of trains in an IRE burst or sequence of trains, delay between trains, selected electrodes of a multi-electrode catheter to be energized by a defined sequence, and times of energization of a train.

Similarly, multichannel radiofrequency (RF) ablation using a multi-electrode catheter involves selection of multiple parameters (e.g., power, duration, temperature limit, electrodes to be used, bi-polar or unipolar setting, etc.).

While a developer may set all of the parameters, or ranges for these parameters, for any given procedure, the large number and inter-relation of the parameters requires the developer to have a good knowledge of the conditions and limitations associated with each of the parameters. Even with this knowledge, setting all parameter values is time consuming and prone to errors.

In practice, existing tools, such as a preferences menu, do not enable a user to prepare a fully optimized ablation protocol. As a result, valid protocols that are probably best suited for the task are not used because they are too complicated to define. Thus, high-end ablation systems and catheters are not utilized in a way that fully exploits their advantages.

Embodiments of the present invention that are described hereinafter provide an ablation programming language that a developer provides, including automatic logic and an editor for a user to write scripts with. For the sake of clarity, the embodiments described herein refer mainly to IRE. The disclosed techniques, however, are applicable in a similar manner to any other suitable type of ablation, e.g., RF ablation.

In some embodiments, the user uses the editor to write a script to generate a given IRE procedure. The programming language includes definitions of IRE parameters, as well as their possible values and limitations. Typically, the IRE programming language provides a wide range of allowable values, and the user selects in the script a more limited range. In addition, each parameter is defined using the provided language syntax. IRE pulses are generated and connected to electrodes of a catheter according to the script.

The developer typically generates one or more graphic user interfaces (GUIs) having the parameters, together with the script written using programming syntax for a given procedure. Using the script, the one or more GUIs, such as one for the IRE protocol parameters and another for system configuration, are adjusted, to allow for user further adjustments without a need to revise the script itself. For example, the user can use interactive GUIs to adjust the IRE protocol parameters and the system configuration.

In an embodiment, a method is provided that comprises, for subsequent use with electrodes of a catheter placed in contact with tissue in an organ, generation of a syntax configured to define commands for (i) setting irreversible electroporation (IRE) protocol parameters and values, (ii) setting a configuration of an IRE system, (iii) applying automatic logic that relates the protocol parameters and values to the configuration of an IRE system, and (iv) one or more user interfaces (GUIs) showing parameters of the IRE protocol and the system configuration. Using the language, a script is generated that is configured to apply a set of the commands, the automatic logic to generate the IRE protocol, and a compatible system configuration. Using the script, one or more of the GUIs are adjusted to show parameters of the IRE protocol and the system configuration. Using the one or more GUIs, the IRE protocol parameters and/or the system configuration, and respective values, are set and/or adjusted.

The disclosed technique therefore enables flexible configuration of IRE protocols and IRE system configurations, without the risk of applying an erroneous protocol or system configuration. To this end, the automatic logic typically comprises a set of rules (e.g., relations) for ablation parameters and system configuration that the one or more GUIs operate (e.g., implement). For example, the GUIs can offer adjustments that are known not to violate interdependencies and limits of IRE protocol values and of system configuration values allowed by the automatic logic.

As an example of the one or more GUI-allowable selections, each IRE channel, typically out of multiple channels (e.g., tens of channels of an IRE generator), is assigned particular pulse parameters, such as of the pulse sequence and waveform, while considering constrains related to pulses from other channels in spatial vicinity (e.g., channels that involve one or more neighboring electrodes of the multi-electrode catheter).

As another example (relating to RF ablation) of one or more GUI-allowable selections, each RF channel, typically out of multiple channels (e.g., tens of channels of an RF generator), is assigned particular RF parameters, such as of the power and frequency, while considering constrains related to, for example, RF power from other channels in spatial vicinity.

By offering a set of commands and automatic logic to generate a wide range of valid IRE protocols and/or RF protocols and system configurations, IRE (or RF) ablation procedures, for example using a multi-electrode catheter in a cardiac chamber, can be accurately set to meet any given clinical case, thereby increasing clinical efficacy and improving safety of IRE (or RF ablation) procedures.

SYSTEM DESCRIPTION

FIG. 1 is a schematic, pictorial illustration of a catheter-based irreversible electroporation (IRE) system 20, in accordance with an exemplary embodiment of the present invention. System 20 comprises a catheter 21, wherein a shaft 22 of the catheter 21 is inserted by a physician 30 through the vascular system of a patient 28 through a sheath 23. The physician then navigates a distal end 22a of shaft 22 to a target location inside a heart 26 of the patient.

Once distal end 22a of shaft 22 has reached the target location, physician 30 retracts sheath 23 and expands balloon 40, typically by pumping saline into balloon 40. Physician 30 then manipulates shaft 22 such that multiple electrodes 50 disposed on the balloon 40 catheter engage an interior wall of a PV ostium 51 to apply high-voltage IRE pulses via multiple electrodes 50 to ostium 51 tissue.

While a balloon catheter is shown, the disclosed embodiments hold for any multi-electrode catheter, such as a basket, multi-arm, or loop catheter. Some of these catheters have as many as a few hundred disposed ablation electrodes that can be managed by the disclosed embodiments for a protocol generation script and user interface.

As seen in inset 25, distal end 22a is fitted with an expandable balloon 40 comprising multiple equidistant smooth-edge IRE electrodes 50. Due to the flattened shape of the distal portion of balloon 40, the distance between adjacent electrodes 50 remains approximately constant even where electrodes 50 cover the distal portion. Balloon 40 configuration therefore allows more effective (e.g., with approximately uniform electric field strength) electroporation between adjacent electrodes 50 while the smooth edges of electrodes 50 minimize unwanted thermal effects.

In the embodiment described herein, catheter 21 may be used for any suitable diagnostic and/or therapeutic purpose, such as electrophysiological sensing and/or the aforementioned IRE isolation of PV ostium 51 tissue in left atrium 45 of heart 26.

The proximal end of catheter 21 is connected to a console 24 comprising an IRE pulse generator 38 configured to apply the IRE pulses between pairs of electrodes 50. The electrodes are connected to IRE pulse generator 38 by electrical wiring running in shaft 22 of catheter 21. A memory 48 of console 24 stores IRE protocols comprising IRE pulse parameters, such as peak bipolar voltage and pulse width.

Console 24 comprises a processor 41, typically a general-purpose computer, with suitable front end and interface circuits 37 for receiving signals from catheter 21 and from external electrodes 49, which are typically placed around the chest of patient 26. For this purpose, processor 41 is connected to external electrodes 49 by wires running through a cable 39.

During a procedure, system 20 can track the respective locations of electrodes 50 inside heart 26, using the Active Current Location (ACL) method, provided by Biosense-Webster (Irvine California), which is described in U.S. Pat. No. 8,456,182, whose disclosure is incorporated herein by reference.

In other embodiments, physician 30 can modify, from a graphical user interface GUI 47 on a display 46, any of the parameters of the protocol and the ablation system configuration. For example, the user may decide whether or not to use neighboring electrodes, a back patch, etc. GUI 47 may be operated with any suitable type of input device, e.g., a keyboard, a mouse, and a touchscreen.

In the shown embodiment, GUI 47 includes GUIs 300 and 400 that were generated by the disclosed IRE language, and are used with a script editor (not shown) to show and adjust an IRE protocol and related system configuration.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated algorithm as disclosed herein, including in FIG. 2, which enables processor 41 to perform the disclosed steps, as further described below. In particular, processor 41 is configured to command IRE pulse generator 38 to output IRE pulses according to a treatment protocol that processor 41 uploads from memory 48.

Syntax for Generating Ire Protocols and Related System Configurations

FIG. 2 is a block diagram schematically showing a system 200 configured to generate a script 205 and a graphical user interface (GUI) 206, using an IRE programming language 202, in accordance with an exemplary embodiment of the present invention.

As seen, system 200 comprises a memory 208, e.g., memory 48 of system 20 of FIG. 1, which stores IRE programming language 202. Language 202 comprises IRE parameters and automatic logic (e.g., a set of relations or rules for ablation parameters and system configuration, the interdependencies and limits of IRE protocol values, and system configuration values). IRE programming language 202 also holds commands for generating one or more GUIs 206. Memory 208 may further store an editor 204 to enable using the commands. In other cases, any suitable text editor can be used, in which case a dedicated editor may not be provided in memory 208.

A processor 210 of system 200, e.g., processor 41 of system 20, uses a developer interface 212 (e.g., on display 46 of system 20) to apply, using editor 204, IRE script 205 that was generated using programming syntax 203.

Script 205 adjusts the one or more initial GUIs 206 into respective actual GUIs 216. For example, the GUI may be adjusted to show a relevant number of channels (e.g., 16, 64, or 92 channels), depending on the multi-electrode catheter used.

GUIs 216 are used, for example by physician 30, to enter the IRE protocol values and the system configuration. Typically, with regard to system configuration, these values affect generator 38 settings and how catheter 21 is used (e.g., electrode connection layout).

For example, as shown in FIG. 2, language 202 provides a command line PULSE.WIDTH=1/20/ELEC, meaning a user can adjust (e.g., select) the range of pulse width between 1 μSec and 20 μSec. As further seen, using script 205 the user adjusts the range to be between 1 μSec and 3 μSec, as can be entered in one of GUIs 216.

As another example, language 202 provides a command line PULSE.DELAY=0.2/1.5/ELEC, meaning a user can adjust the range of inter-pulse delay between 0.2 μSec and 1.5 μSec. As further seen, using script 205 the user adjusts the range to be between 0.5 μSec and 1 μSec, as can be entered in one of GUIs 216.

Additionally or alternatively, language 202 may provide any other suitable commands, e.g., using a command-line or otherwise.

The script and use of language shown in FIG. 2 is depicted purely by way of example. In alternative embodiments, any other suitable scripts can be used, such as devised for an RF system, using the same script generation technique.

GUI for Setting and Adjusting Ire Protocol Values and System Configuration

FIG. 3 is an example of GUI 300 for configuration of system 20, where the GUI was generated using IRE programming language 202 of FIG. 2, in accordance with an exemplary embodiment of the present invention.

In the depicted embodiment, a user can move between windows of different "slots" 302, where a slot is a time period for a given single train of pulses. The figure shows one example slot denoted "slot 1".

For each slot 302, different settings can be defined for each channel 304. In this example, there are 6 channels.

By way of example, there are five parameters per channel 304, and these define the system configuration per the slot by being checked or unchecked.

The five shown parameters are:
1. Fast Output: defines whether a channel is active in the current slot
2. Slow output: defines whether an electrode is connected to the channel
3. Backpatch: defines whether a channel is connected to another channel internally
4. Neighbor: defines whether a channel is connected to an adjacent electrode
5. Polarity swap: defines the positive or negative polarity of the pulse In the example shown, channels 1 to 4 of Slot 1 are defined as connected to the output electrode and active. Channels 1 to 4 are also connected internally with positive polarity. Channels 5 to 8 are defined as connected to the output but inactive. Channel 9 is defined as connected to the output electrode, active and also connected to channels 1 to 4 internally with negative polarity. Channel 10 is totally disconnected. In a similar manner, other slots can be configured in their respective windows.

Figures 4, 5:
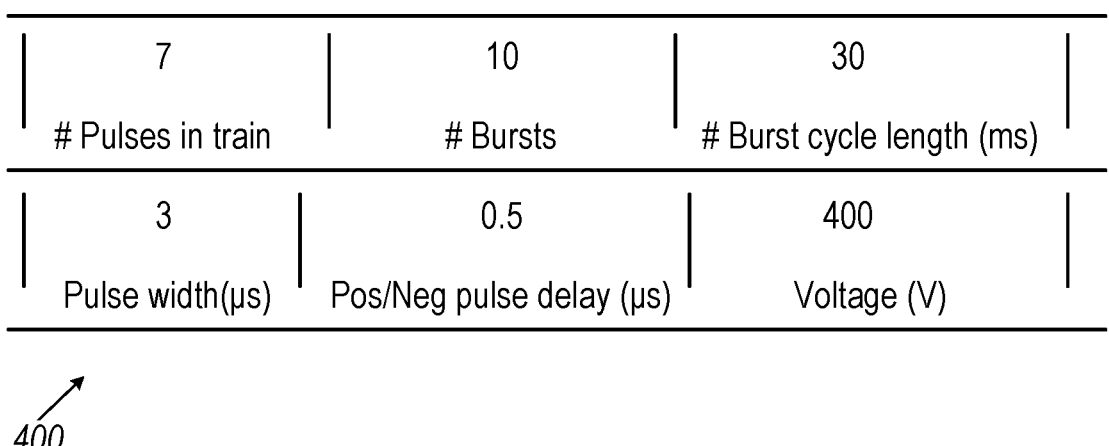
FIG. 4 is an example of a GUI for specifying IRE protocol parameters, where the GUI was generated using the programming language of FIG. 2, in accordance with an exemplary embodiment of the present invention.
FIG. 5 is a flow chart that schematically illustrates a method for setting up an IRE protocol and a system configuration using the IRE programming language and script of FIG. 2, and GUIs of FIGS. 3 and 4, in accordance with an exemplary embodiment of the present invention.

FIG. 4 is an example of a GUI 400 for specifying IRE protocol parameters, where the GUI is generated using the IRE programming language 202 of FIG. 2, in accordance with an exemplary embodiment of the present invention.

In the shown example, pulse width is set to 3 µs. Automated logic allows the pulse width to be between 1 µs and 20 µs. The delay between pulses is set to 0.5 µs. The automated logic allows this delay to be between 0.2 µs and 1.5 µs. The number of pulses in a train is set to 7. The number of trains is set to 10. The delay between trains is set to 30 ms. The pulse amplitude is set to 400 V.

The GUIs shown in FIGS. 3 and 4 are depicted purely by way of example. In alternative embodiments, any other suitable GUIS can be used, such as devised for an RF system, using the same GUI generation technique.

Method for Generating Ire Protocols and Related System Configurations

FIG. 5 is a flow chart that schematically illustrates a method for setting up an IRE protocol and system configuration using IRE programming language 202 and script 205 of FIG. 2, and GUIs 300 and 400 of FIGS. 3 and 4, in accordance with an exemplary embodiment of the present invention.

The algorithm, according to the presented embodiment, carries out a process that begins with a user directing processor 210 to upload IRE parameters and automatic logic 203 from memory 208, at an uploading step 502.

Next, with an offline processor 210 displaying a developer interface 212, the user generates IRE language 202, at a language syntax generation step 504.

Next, with processor 210 displaying a developer interface 212, the user generates script 205, at a script generation step 505.

Next, using script 205, the user generates GUIs 300 and 400, at GUIs generation step 506. GUIs 300 and 400 show system configuration and IRE protocol parameters, respectively.

Finally, using GUIs 300 and 400, the user enters (e.g., adjusts) the system configuration and/or the IRE protocol values, at an ablation preparatory step 508.

At this point, the user can operate system 20 to perform the ablation the user planned on steps 502-508.

While the workflow of FIG. 5 describes setting up an IRE protocol and IRE system configuration, the flowchart holds, mutatis mutandis, for setting up an RG protocol and RF system configuration.

Although the embodiments described herein mainly address cardiac applications, the methods and systems described herein can also be used in other medical applications, such as in neurology and otolaryngology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for generating ablation protocols and system configurations, the method comprising:
 generating an ablation programming language, which defines commands for (i) setting ablation protocol parameters and respective values, (ii) setting a configuration of an ablation system, (iii) applying automatic logic that relates the ablation protocol parameters and the respective values to the configuration of the ablation system, and (iv) generating one or more graphical user interfaces (GUIs) configured to:
 display one or more of the ablation protocol parameters and the configuration of the ablation system;
 restrict user input values for adjusting the ablation protocol parameters or the configuration of the ablation system to predefined ranges enforced by the automatic logic; and
 receive the user input values for setting the ablation protocol parameters or the configuration of the ablation system to the predefined ranges enforced by the automatic logic; and
 providing the ablation programming language for subsequent use with the ablation system to perform an ablation.

2. The method according to claim 1, wherein the automatic logic specifies one or more interdependencies between the respective values of the ablation protocol parameters.

3. The method according to claim 1, wherein the automatic logic specifies one or more limits on the respective values of the ablation protocol parameters.

4. The method according to claim 1, wherein the ablation programming language is configured for use during the ablation, and wherein the ablation is one of irreversible electroporation (IRE) and radiofrequency (RF) ablation.

5. A computer software product comprising a tangible non- transitory computer-readable medium in which program instructions are stored, which the program instructions, when read by one or more processors, cause the one or more processors to:

generate an ablation programming language, which defines commands for (i) setting ablation protocol parameters and respective values, (ii) setting a configuration of an ablation system, (iii) applying automatic logic that relates the ablation protocol parameters and the respective values to the configuration of the ablation system, and (iv) generating one or more graphical user interfaces (GUIs) configured to:

display one or more of the ablation protocol parameters and the configuration of the ablation system;

restrict user input values for adjusting the ablation protocol parameters or the configuration of the ablation system to predefined ranges enforced by the automatic logic; and receive the user input values for setting the ablation protocol parameters or the configuration of the ablation system to the predefined ranges enforced by the automatic logic; and provide the ablation programming language for subsequent use with the ablation system to perform an ablation.

\* \* \* \* \*